(12) United States Patent
Terashi et al.

(10) Patent No.: US 8,109,888 B2
(45) Date of Patent: Feb. 7, 2012

(54) MEDICAL GUIDE WIRE

(75) Inventors: Tsuyoshi Terashi, Tokyo (JP); Seiji Shimura, Tokyo (JP)

(73) Assignee: FMD Co., Ltd., Tokyo (JP)

(*) Notice: Subject to any disclaimer, the term of this patent is extended or adjusted under 35 U.S.C. 154(b) by 148 days.

(21) Appl. No.: 12/617,456

(22) Filed: Nov. 12, 2009

(65) Prior Publication Data

US 2010/0057053 A1 Mar. 4, 2010

Related U.S. Application Data

(62) Division of application No. 11/756,671, filed on Jun. 1, 2007, now Pat. No. 7,637,874.

(30) Foreign Application Priority Data

Jun. 2, 2006 (JP) .................... 2006-155019

(51) Int. Cl.
*A61B 5/00* (2006.01)
(52) U.S. Cl. ..................................... 600/585
(58) Field of Classification Search .................. 600/585, 600/434, 435
See application file for complete search history.

(56) References Cited

U.S. PATENT DOCUMENTS

| | | | | |
|---|---|---|---|---|
| 4,619,274 A | * | 10/1986 | Morrison | 600/585 |
| 4,748,986 A | * | 6/1988 | Morrison et al. | 600/585 |
| 4,811,743 A | * | 3/1989 | Stevens | 600/585 |
| 4,873,983 A | * | 10/1989 | Winters | 600/434 |
| 5,354,257 A | | 10/1994 | Roubin et al. | |
| 5,363,847 A | * | 11/1994 | Viera | 600/434 |
| 5,402,799 A | * | 4/1995 | Colon et al. | 600/585 |
| 6,139,511 A | * | 10/2000 | Huter et al. | 600/585 |
| 6,648,837 B2 | * | 11/2003 | Kato et al. | 600/585 |
| 6,669,652 B2 | * | 12/2003 | Anderson et al. | 600/585 |
| 7,278,974 B2 | | 10/2007 | Kato | |
| 2002/0082524 A1 | * | 6/2002 | Anderson et al. | 600/585 |
| 2002/0095102 A1 | * | 7/2002 | Winters | 600/585 |
| 2002/0198468 A1 | * | 12/2002 | Kato et al. | 600/585 |
| 2005/0096568 A1 | * | 5/2005 | Kato | 600/585 |
| 2005/0148902 A1 | * | 7/2005 | Minar et al. | 600/585 |
| 2005/0203442 A1 | * | 9/2005 | Kato | 600/585 |
| 2006/0167384 A1 | * | 7/2006 | Kato | 600/585 |

FOREIGN PATENT DOCUMENTS

| | | |
|---|---|---|
| JP | 5916649 U | 2/1984 |
| JP | 4-309368 | 10/1992 |

* cited by examiner

*Primary Examiner* — Max Hindenburg
*Assistant Examiner* — Michael C Stout
(74) *Attorney, Agent, or Firm* — Sughrue Mion, PLLC

(57) ABSTRACT

A medical guide wire includes a flexible long core. A core elongated component is disposed to extend forwards from the core, and has a tapered shape. A helical coil is disposed about the core elongated component, secured by attachment of a coil distal end and a coil proximal end to the core elongated component. The helical coil includes an equiradial coil portion having the coil proximal end, disposed at a portion of the core elongated component on a side of the core. A diameter decreasing coil portion has the coil distal end, extends forwards from the equiradial coil portion, has a decreasing diameter, and has a length 25 mm or more. A diameter ratio D1/D2 of the diameter decreasing coil portion is 1.22-2.31, where D1 is a proximal end diameter of the diameter decreasing coil portion, and D2 is a distal end diameter of the diameter decreasing coil portion.

4 Claims, 9 Drawing Sheets

MEDICAL GUIDE WIRE

CROSS-REFERENCE TO RELATED APPLICATIONS

This is a divisional of application Ser. No. 11/756,671 filed Jun. 1, 2007, which claims priority to JP 2006-155019 filed Jun. 2, 2006. The entire disclosure of the prior application, application Ser. No. 11/756,671, is hereby incorporated by reference.

BACKGROUND OF THE INVENTION

1. Field of the Invention

The present invention relates to a medical guide wire. More particularly, the present invention relates to a medical guide wire for use in treatment of blood vessels of constriction, for example a coronary artery, an artery of lower extremities or the like.

2. Description Related to the Prior Art

A medical guide wire is used for inserting a catheter into a blood vessel for various purposes. A flexible catheter of a very small width is inserted with the medical guide wire for the purpose of angiography of vessels. Otherwise, a balloon catheter is inserted in an occlusion of a coronary artery for intravascular treatment. The use of the medical guide wire is for safety and reliability. The medical guide wire is required to have flexibility and buckling resistant property for the purpose of insertion in vessels of complicated curved paths or vessel branches. Also, the medical guide wire should have steerability and suitable rigidity of torsion in order to operate the guide wire tip in a vessel by extracorporeally rotating the proximal end of the medical guide wire. JP-U 59-016649 and U.S. Pat. No. 5,354,257 (corresponding to JP-A 4-309368) disclose the medical guide wire including a core and a helical coil. The core has a very small diameter. The helical coil is wound about the core, has a decreasing diameter, so the guide wire tip of the medical guide wire has a tapered shape.

In FIG. 12, a total occlusive lesion 100 in a coronary artery is illustrated. According to gradual organization of thrombus, an occlusion 102 in a blood vessel 101 becomes tissue. Organization is rather early on ends of the occlusion 102 in contrast with slowness in organization at the middle point of the occlusion 102. As a result, portions of plaque or hard tissue 103 occur in the middle path in the blood vessel 101. For the total occlusive lesion 100, a medical guide wire 105 for intravascular treatment is used to penetrate the total occlusive lesion 100 by rotating forwards and backwards, the medical guide wire 105 including a flexible helical coil disposed at the guide wire tip, and having strands spaced from one another.

When the guide wire tip of the medical guide wire 105 is rotated forwards and backwards, a cavity called a false lumen 106 is created in a different direction by drilling of the medical guide wire 105. The false lumen 106 may be enlarged, from which the medical guide wire 105 cannot move away. A true lumen cannot be reached as intended in the vessel. In FIG. 13, a recently used method of penetration of the total occlusive lesion 100 is illustrated. A medical guide wire 110 for intravascular treatment has a rigid tip, and can penetrate the total occlusive lesion 100 even with the plaque or hard tissue 103 contained in the total occlusive lesion 100. Conception of improving the medical guide wire 110 has been developed in view of suitability for this method. If the rigidity of the guide wire tip is too high, steerability of the medical guide wire 110 will be low because of low flexibility of the guide wire tip.

In FIG. 14, an encircling calcified lesion 115 is created as a result of organizing thrombus. Plaque or hard tissue 116 of the calcified lesion 115 is still more difficult to penetrate with a tool. There a pair of ends 118 and 119 in a cup shape disposed on the sides of the occlusion of the calcified lesion 115. The end 118 has a greater thickness than the end 119. When a medical guide wire 120 for intravascular treatment passes through the blood vessel, the guide wire tip buckles in the vicinity of the end 118, which cannot be penetrated. If the medical guide wire 120 can penetrate, the guide wire tip is likely to offset from the middle of the end 119. The guide wire tip may erroneously reach a false lumen 121, because the middle of the end 119 is convexly formed. No known structure of the guide wire tip can penetrate successfully.

SUMMARY OF THE INVENTION

In view of the foregoing problems, an object of the present invention is to provide a medical guide wire for use in treatment of blood vessels with high steerable property and also penetrable property.

In order to achieve the above and other objects and advantages of this invention, a medical guide wire includes a flexible long core. A core elongated component is disposed to extend forwards from an end of the core, and has a tapered shape. A helical coil is disposed about the core elongated component, secured by attachment of a coil distal end and a coil proximal end to the core elongated component. The helical coil includes an equiradial coil portion having the coil proximal end, disposed at a portion of the core elongated component on a side of the core. A diameter decreasing coil portion has the coil distal end, is disposed to extend forwards from the equiradial coil portion, has a decreasing diameter, and has a length equal to or more than 25 mm. A middle connector is disposed at a distance equal to or less than 50 mm from the coil distal end, for attaching the helical coil to the core elongated component. The helical coil has a coil filament with strands tightly wound in a range from the coil distal end to the middle connector. A diameter ratio D1/D2 of the diameter decreasing coil portion is equal to or more than 1.22 and equal to or less than 2.31, where D1 is a diameter of the diameter decreasing coil portion on a side of the coil proximal end, and D2 is a diameter of the diameter decreasing coil portion on a side of the coil distal end. The core elongated component and the helical coil satisfy a condition of $d2 \geq t$, where d2 is a diameter of a distal end of the core elongated component, and t is a filament diameter of the coil filament of the helical coil.

Furthermore, a guide wire tip is positioned at a distal end, and having one portion of the core elongated component and the coil distal end of the helical coil attached to the core elongated component.

The middle connector is positioned on a proximal side from a point defined between the diameter decreasing coil portion and the equiradial coil portion. A first length ratio L1/L2 of the helical coil is equal to or more than 1, where L1 is a length of the diameter decreasing coil portion, and L2 is a length of the equiradial coil portion extending to the middle connector.

In one preferred embodiment, one end of the diameter decreasing coil portion nearer to the equiradial coil portion is disposed at the middle connector.

The helical coil further includes an equiradial coil end, disposed to extend forwards from the diameter decreasing coil portion, for constituting the guide wire tip. A second length ratio L1/L3 of the helical coil is equal to or more than 3.1 and equal to or less than 24, where L1 is a length of the diameter decreasing coil portion, and L3 is a length of the equiradial coil end.

The second length ratio L1/L3 of the helical coil is equal to or more than 3.1 and equal to or less than 7.3.

The diameter D1 is equal to or less than 0.360 mm in a range from the guide wire tip to the middle connector. The diameter ratio D1/D2 is equal to or more than 1.22 and equal to or less than 1.85.

In the range from the guide wire tip to the middle connector, the helical coil and the core elongated component satisfy conditions of:

$$t \leq d2 \leq (D2-2 \times t)$$

$$t < d1 \leq (D1-2 \times t)$$

$$1.10 \leq d1/d2 \leq 2.64.$$

In the range from the guide wire tip to the middle connector, the helical coil and the core elongated component satisfy conditions of:

$$t \leq d2 \leq (D2-2.5 \times t)$$

$$t < d1 \leq (D1-2.5 \times t).$$

In another preferred embodiment, the diameter D1 is equal to or less than 0.450 mm in a range from the guide wire tip to the middle connector. The diameter ratio D1/D2 is equal to or more than 1.52 and equal to or less than 2.31.

In the range from the guide wire tip to the middle connector, the helical coil and the wire haft satisfy conditions of:

$$t \leq d2 < (D2-2 \times t)$$

$$t < d1 \leq (D1-2 \times t)$$

$$1.10 \leq d1/d2 \leq 3.68.$$

At least the diameter decreasing coil portion in the helical coil is produced from radiopaque material.

Furthermore, an equiradial helical coil part is secured to the equiradial coil portion of the helical coil, and disposed to extend to a proximal side.

The equiradial helical coil part is attached to the helical coil by the middle connector.

The helical coil further includes a lubricant coating overlaid on a peripheral surface of at least the diameter decreasing coil portion, having lubricating property when wetted.

In one preferred embodiment, the diameter decreasing coil portion has a diameter decreasing in a range extending to the guide wire tip.

The core elongated component includes an equiradial shaft portion disposed inside the equiradial coil portion. A tapered shaft portion is disposed to extend from the equiradial shaft portion and inside the diameter decreasing coil portion, and has a diameter decreasing toward the guide wire tip.

In still another preferred embodiment, the diameter decreasing coil portion extends toward a proximal side and about the equiradial shaft portion.

In one preferred embodiment, the helical coil includes an equiradial coil end disposed to extend from the diameter decreasing coil portion to the guide wire tip. The core elongated component includes an equiradial shaft end disposed to extend from the tapered shaft portion and inside the equiradial coil end.

The helical coil is so disposed that a space of a predetermined thickness is defined about the core elongated component in a range offset from the middle connector.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
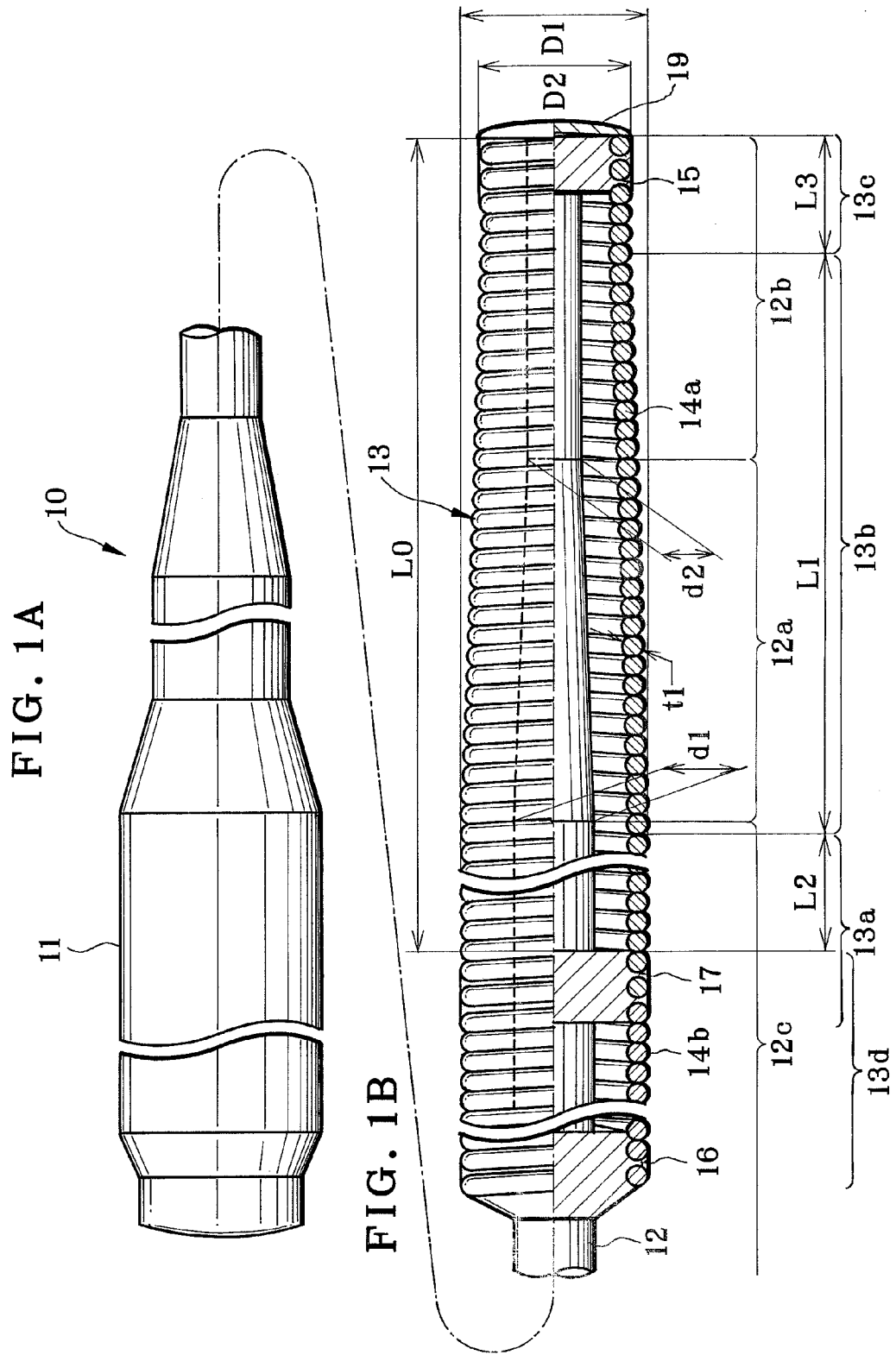
FIG. 1A is a plan illustrating a core of a medical guide wire.
FIG. 1B is a horizontal section illustrating a core elongated component and a helical coil of the medical guide wire.

In FIGS. 1A and 1B, a medical guide wire 10 for intravascular treatment includes a core 11, a core elongated component 12 at a distal end, and a tubular winding or helical coil 13. The core 11 is long and flexible. The core elongated component 12 extends from a distal end of the core 11, and has a smaller diameter in a tapered shape. The helical coil 13 is attached to the core elongated component 12. Examples of materials for the core 11 are SUS 304 steel, Ni—Ti alloy and the like. Examples of materials for the helical coil 13 are SUS 304 steel, gold, platinum, tungsten or other radiopaque substances. A length of the medical guide wire 10 is 1,400-3,000 mm. A length of the helical coil 13 is 30-300 mm. A proximal end of the core 11 is coated with a covering layer of a fluorocarbon resin or the like. An outer periphery of the helical coil 13 is coated with a first layer of polyurethane or other resin, and a second layer of hydrophilic polymer for lubricating property at the time of being wetted.

A tapered shaft portion 12a of transition is included in the core elongated component 12, and has a decreasing diameter. An equiradial shaft end 12b or ribbon extends from the tapered shaft portion 12a with a first diameter at a guide wire tip. A small diameter shaft portion 12c of transition extends from the tapered shaft portion 12a on the proximal side with a second diameter.

The helical coil 13 includes an equiradial helical coil part 13d on a proximal side, an equiradial coil portion 13a on the proximal side, and a diameter decreasing coil portion 13b of transition. If required, the helical coil 13 also has an equiradial coil end 13c at a guide wire tip. The helical coil 13 is set on the core elongated component 12 by receiving its insertion loosely. The equiradial helical coil part 13d and the equiradial coil portion 13a are positioned on the proximal side of the core elongated component 12. The diameter decreasing coil portion 13b is positioned on the distal side of the core elongated component 12. Then the helical coil 13 is fixedly secured to the core elongated component 12 with paraffin wax. Three positions are determined for fixation with the paraffin wax. A distal end connector 15 at a guide wire tip is located on the distal side of the helical coil 13. A proximal end connector 16 is located on the proximal side of the helical coil 13. A middle connector 17 of paraffin wax similarly is disposed between the end connectors 15 and 16.

In the helical coil 13, a coil filament 14a of alloy is wound to constitute the equiradial coil end 13c, the diameter decreasing coil portion 13b, and a region of the equiradial coil portion 13a extending to the middle connector 17, and is produced from alloy containing gold, platinum, tungsten or other radiopaque substance as main component. The coil filament 14a is wound by a spring coil winder known in the art in a tightly wound coil. The helical coil of the coil filament 14a may be spaced from the core elongated component with a greater diameter, or may be fitted with the core elongated component at an equal diameter. A coil filament 14b is wound to constitute the equiradial helical coil part 13d extending from the middle connector 17 to the proximal side, and is produced from general-purpose material, such as SUS 304 steel. An amount of radiopaque substances is reduced by the combined use of the steel or the like, to reduce the manufacturing cost, while radiopaque substances are typically expensive. The middle connector 17 attaches the coil filament 14b to the coil filament 14a with paraffin wax. At least one turn of the coil filament 14b is helically coupled with at least one turn of the coil filament 14a at the middle connector 17 before attachment with the paraffin wax. Note that the coil filament 14b in the helical coil 13 can be different from the coil filament 14a in the filament diameter in place of the material. Various methods are available to produce the helical coil 13. For example, a first wire of radiopaque material is attached by welding to a second wire of a radiolucent material. The first and second wires are then coiled to form the helical coil 13. Otherwise, a wire of a single material can be wound in a coiled form. Irrespective of the methods, however, it is important to keep the helical coil 13 tightly attached by the middle connector 17 at a predetermined distance.

Note that a meaning of the term of tight winding in this specification includes a state of complete contact of all strands of the coil filament 14a wound in the helical coil 13, and also a state of apparently tight contact of strands of the coil filament 14a as viewed by human eyes. Strands of the coil filament 14a contacting one another as viewed by human eyes may be separate from one another if observed in enlargement with a lens or the like. The term of the tight winding in this specification is also used to include a state of existence of a space between strands of the coil filament 14a equal to or less than 9% relative to the filament diameter t1 (mm) of the coil filament 14a. Note that the space between strands of the coil filament 14a can be preferably equal to or less than 5% relative to the filament diameter t1 (mm) of the coil filament 14a, and equal to or less than 3%.

As important features of the helical coil 13, the diameter decreasing coil portion 13b is included. A portion extending to the middle connector 17 is formed from a radiopaque material. Note that the entirety of the coil filament 14a may be produced from a radiopaque material according to the invention. However, the partial use of the radiopaque material for portions including the diameter decreasing coil portion 13b is advantageous, because the cost of manufacturing is reduced in consideration of the expensive radiopaque material.

Figure 2:
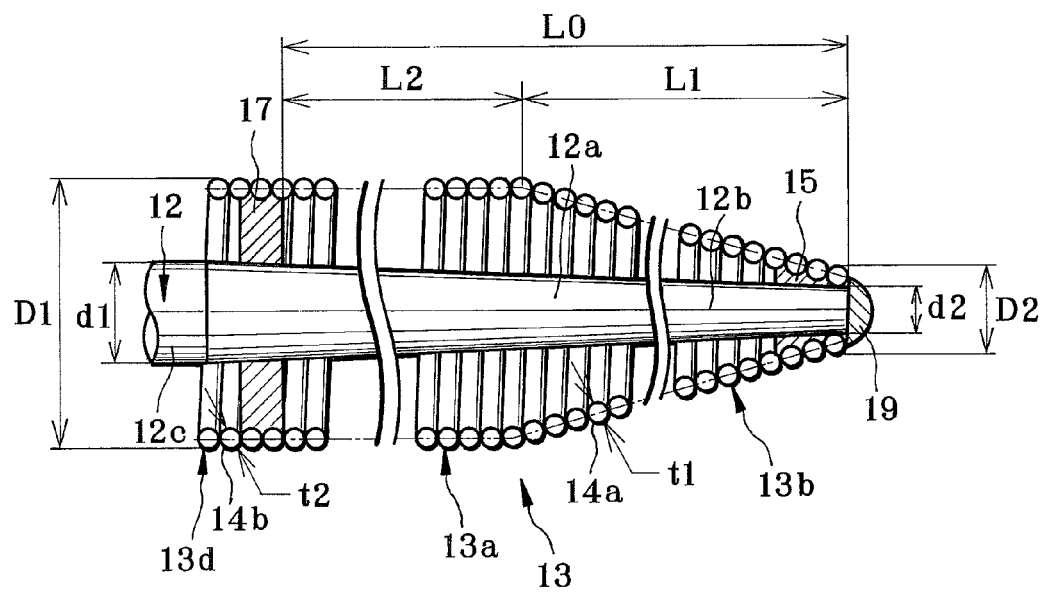
FIG. 2 is an explanatory view in section illustrating each of first, second and third embodiments.

Various preferred embodiments with the core elongated component 12, the helical coil 13 and other portions are hereinafter described. In FIG. 2, a first embodiment is illustrated. The coil filament 14a of platinum has a filament diameter t1 of 0.065 mm, and is wound to define the diameter decreasing coil portion 13b and the equiradial coil portion 13a of the helical coil 13. The coil filament 14b of SUS 304 steel has a filament diameter t2 of 0.060 mm, and is wound by coiling to define the equiradial helical coil part 13d of the helical coil 13 from the middle connector 17 to the proximal side. The equiradial helical coil part 13d is attached to the equiradial coil portion 13a by the middle connector 17 with paraffin wax to obtain the helical coil 13. Note that the equiradial helical coil part 13d on the proximal side may not be wound tightly with a difference from the diameter decreasing coil portion 13b. The proximal end diameter D1 of the helical coil 13 is equal to or less than 0.360 mm. The tapered portion length L1 of the diameter decreasing coil portion 13b is equal to or more than 25 mm. A diameter ratio D1/D2 of the proximal end diameter D1 to the diameter D2 is equal to or more than 1.22 and equal to or less than 1.85. The length L0 from the guide wire tip to the middle connector 17 is 50 mm.

The core elongated component 12 has the distal shaft diameter d2 that is equal to or more than filament diameter t1 of the coil filament 14a, and is shaped with a decreasing diameter in a tapered manner. The first embodiment is constructed as a guide wire for treatment of a coronary artery. Second to tenth embodiments following the first embodiment are disclosed for this common purpose. The diameter of the medical guide wire 10 is extremely small in comparison with its length. Note that the medical guide wire 10 can be hardly depicted in one drawing sheet if a ratio of enlargement is the same in the longitudinal direction as in the radial direction. So the medical guide wire 10 is depicted in a higher factor of enlargement in the radial direction than in the longitudinal direction.

Figure 3:
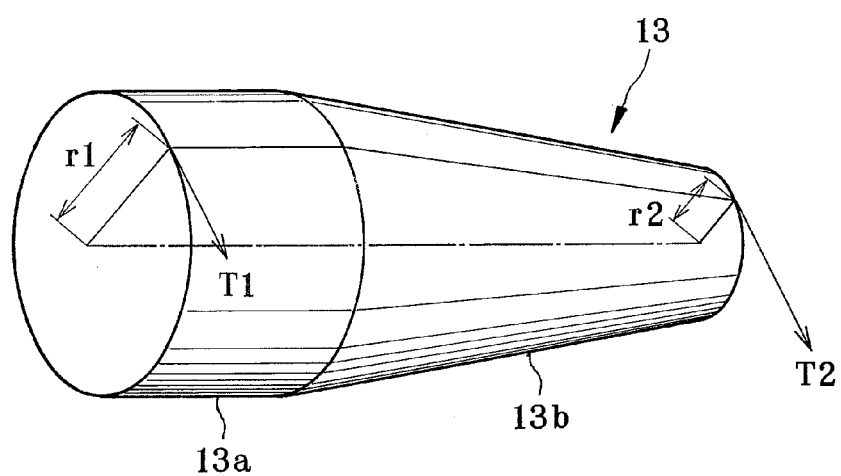
FIG. 3 is a perspective illustrating the first embodiment with indicated parameters of the guide wire related to transmission of rotation.

In the first embodiment having the tapered end portion with tightly wound strands of the helical coil 13, the diameter decreasing coil portion 13b can cause performance of transmission to be higher from the proximal side to the distal side, and also can raise force of penetration or advance. In FIG. 3, torque or rotational force T1 and T2 for the helical coil 13 is determined according to a length ratio r1/r2 of lengths or radii of rotatable portions. As the diameter D1 is 0.360 mm and the diameter D2 is 0.253 mm, rotational transmission of force from the proximal side to the distal side is approximately 1.42 times higher than an example in a regularly helical shape having D1 and D2 of 0.360 mm, because of 0.360/0.253.

Figure 12:
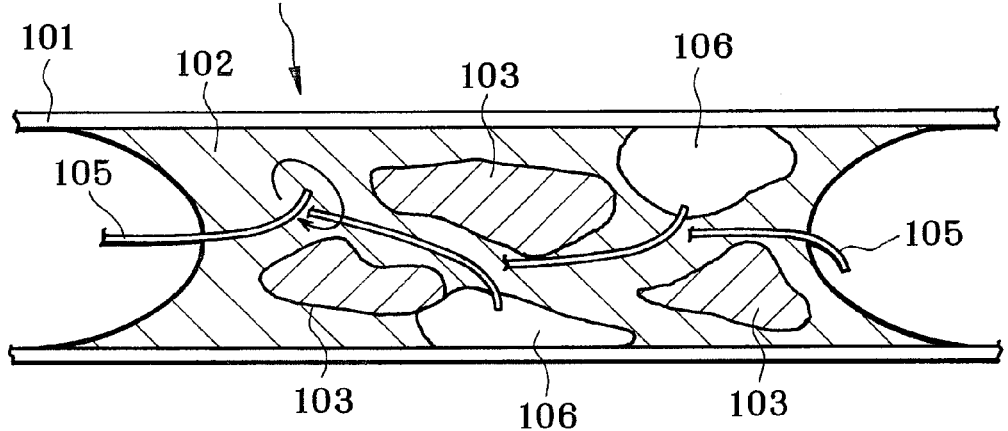
FIG. 12 is a schematic view illustrating the use of a known guide wire for a total occlusive lesion in a coronary artery.
Figure 13:
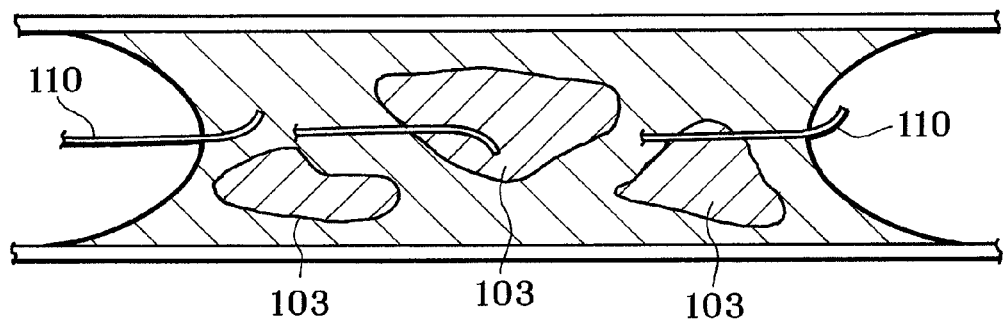
FIG. 13 is a schematic view illustrating the use of the known guide wire for an occlusive lesion with hard plaque.
Figure 14:
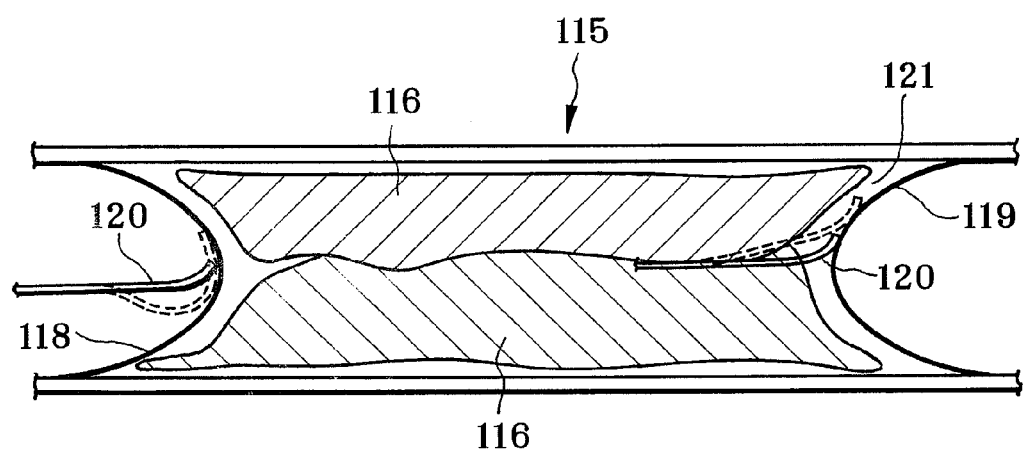
FIG. 14 is a schematic view illustrating the use of the known guide wire for an encircling calcified lesion.

The operation of the helical coil 13 is assumed in a form of a screw. Force P in the axial direction is proportional to a force in the tangential direction. The tangential force is regarded as torsional force. The torsional force of the helical coil 13 is approximately 1.42 times as high as that of a helical coil of which D1 and D2 is 0.360 mm equally. The axial direction force P can be approximately 1.42 times higher. Therefore, ability of penetration can be high with higher performance of transmission of rotation and higher force in the axial direction. High force of penetration is obtained for any of lesions, including a total occlusive lesion 100 of FIG. 12, and a calcified lesion 115 and ends 118 and 119 of the calcified lesion 115 in a cup shape illustrated in FIG. 14.

Spring constants of a fully equiradial helical coil and the helical coil 13 having an equal filament diameter are calculated. As a result, a spring constant of the helical coil 13 is approximately 1.59 times as much as that of the fully equiradial helical coil having the equal filament diameter and having a maximum coil diameter equal between those. Note that a torsion angle of a coil changes inversely proportional to the spring constant. Thus, a torsion angle of the helical coil 13 is small. Therefore, rotational force on the proximal side can be transmitted to the distal side with a high rotational force even with a rotation at a small torsion angle. It is possible in FIGS. 4A-4C that a constriction 30 can be penetrated by the guide wire.

Figure 4A:
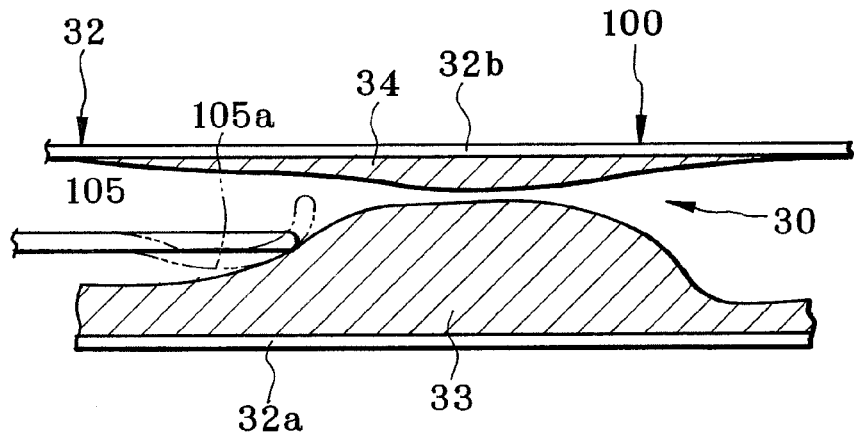
FIG. 4A is a schematic view illustrating a state of the guide wire related to approach to a lesion in a blood vessel.
Figure 4B:
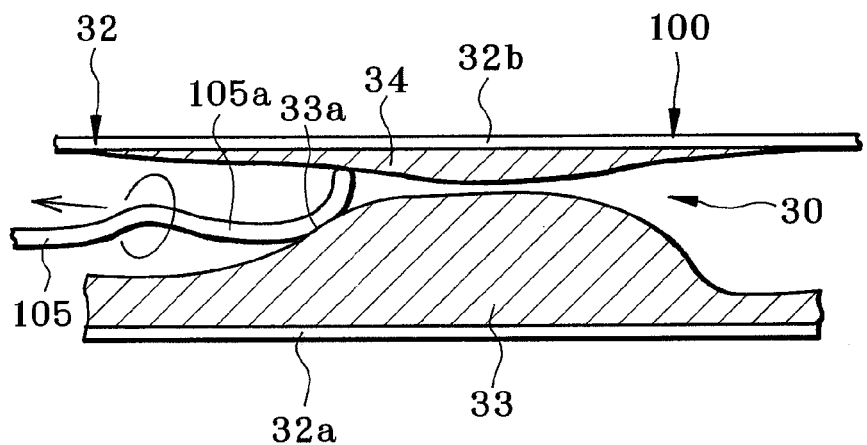
FIGS. 4B and 4C are schematic views illustrating a state of the guide wire passing the lesion.
Figure 4C:
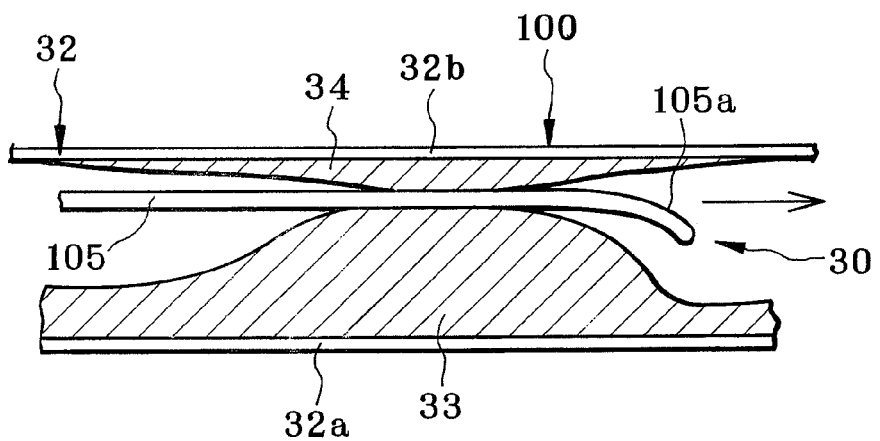

FIGS. 4A-4C illustrate a state of a guide wire tip 105a in the constriction 30 according to a known medical guide wire 105 for intravascular treatment. For example, a blood vessel 32 has the constriction 30. One vessel wall 32a has a large plaque or hard protrusion 33. A second vessel wall 32b has a small plaque or hard protrusion 34, which defines the constriction 30 with the large plaque 33. In FIG. 4B, an inclined surface 33a of the large plaque 33 is pressed by the guide wire tip 105a of the medical guide wire 105, which causes deflection, and is slightly moved back while rotated. In FIG. 4C, the guide wire tip 105a is caused to penetrate the constriction 30 by use of the reaction force of the guide wire tip 105a as a spring.

In FIG. 4B, failure of penetration of the medical guide wire 105 is illustrated. Upon contact with the inclined surface 33a, the guide wire tip 105a becomes buckled due to the bendable property. Spaces between strands of the coil of the medical guide wire 105 are enlarged by particles of plaque, so reaction force of the guide wire tip 105a decreases considerably. Thrusting into the constriction 30 with the reaction force may be unsuccessful.

The helical coil 13 according to the first embodiment has a shape of which the diameter of the distal end decreases in a tapered manner. There is no space between strands owing to the tight winding of the coil filament 14a. Thus, the helical coil 13 can have a high spring constant in comparison with the regular diameter coil spring of which the maximum diameter is the same as that of the helical coil 13. Sufficient reaction force can be ensured by the high spring constant. No gap between the strands will open according to the tight winding, hard pieces of plaque are prevented from entry in or interference with a portion of the coil filament 14a. The shape of the reduced diameter of the distal end is also effective in passage through the constriction 30 by means of the reaction force of the spring.

Figure 5A:
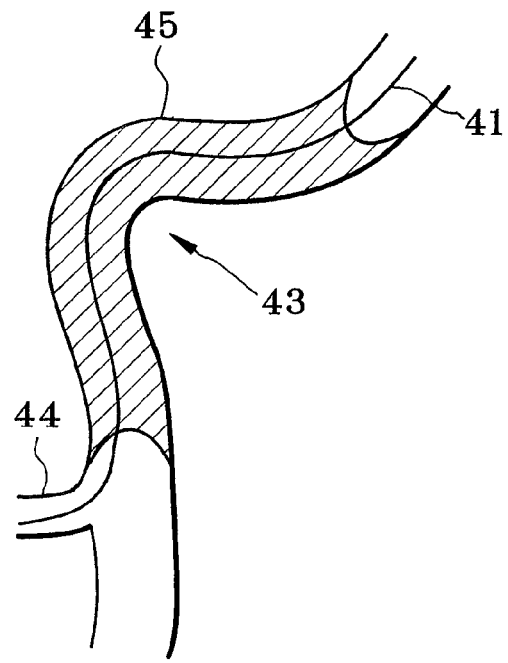
FIG. 5A is a schematic view illustrating a blood vessel and a guide wire for use in a parallel wire technique.
Figure 5B:
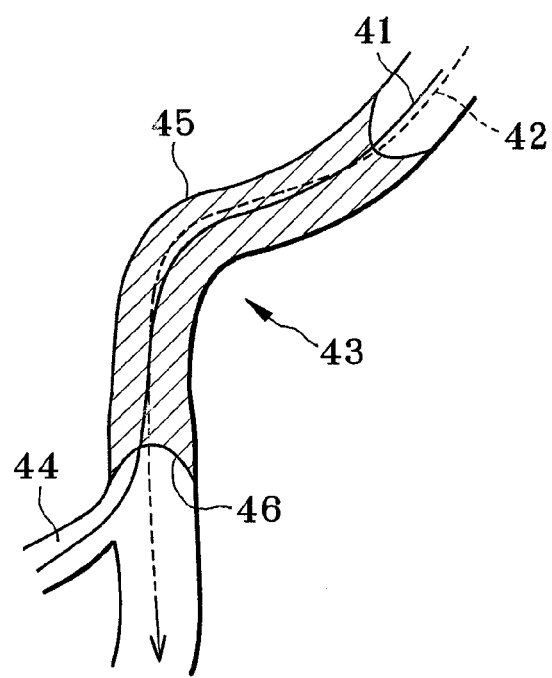
FIG. 5B is a schematic view illustrating the blood vessel and a set of two guide wires in the parallel wire technique.

There is a method referred to as a parallel wire technique of medical guide wires 41 and 42 for intravascular treatment. In FIGS. 5A and 5B, the medical guide wire 41 is inserted in a coronary artery 45. Then the medical guide wire 42 is inserted into the coronary artery 45 by use of the medical guide wire 41 as a guide. A lesion 43 in the coronary artery 45 is penetrated by the medical guide wire 42. A guide wire of the invention can be effectively used as the medical guide wire 42 in use for the second time. It is possible easily to penetrate the lesion 43, specifically a diffuse lesion having a lesion length of 20 mm or more, and a right coronary artery having a bend of a zigzag shape.

In FIG. 5A, the medical guide wire 41 is inserted in a blood vessel branch 44, to extend the coronary artery 45 of a bent shape in a straightened manner. See FIG. 5B. Then the medical guide wire 42 of a second insertion is introduced to the lesion 43 while guided by the medical guide wire 41. As described above, a farther end 46 in a cup shape of the occlusion has a convex shape at the center. Failure is likely to occur with the known guide wire in accessing the middle of the farther end 46, because the guide wire has a soft guide wire tip. Furthermore, a loosely wound helical coil with spaces between strands has a problems in incidental entanglement of the medical guide wire 42 with the medical guide wire 41.

In contrast, the first embodiment has the tapered distal portion, and a small diameter at the guide wire tip. For the penetrability upon handling on the proximal side, a surface pressure of the guide wire tip per unit area of the end surface increases, so performance of penetration is high. The small diameter of the guide wire tip is predetermined according to the filament diameter. Penetration and breakage of the plaque can be efficient and easy. Also, the coil filament 14a in the helical coil 13 is wound with tightly wound strands. Entanglement of the medical guide wire 42 with the medical guide wire 41 can be prevented. Even when a perforation of the vessel occurs, the perforation diameter can be small because of the small diameter of the guide wire tip. The hemostasis is easy in comparison with the state of using the structure having fully equiradial helical coil.

The middle connector 17 with paraffin wax is positioned at a distance of 50 mm or less from the guide wire tip. The length of the diameter decreasing coil portion 13b of the helical coil 13 is set equal to or more than a half of a length from the distal end to the middle connector 17. Thus, attachment of the core 11 to the helical coil 13 with paraffin wax is combined with the tightly wound state of the helical coil 13. It is possible as an effect to prevent widening intervals between the coil filament 14a of the helical coil 13 owing to the middle connector 17 even when the tip of the medical guide wire 10 penetrates into a lesion with hard plaque or tissue. Transmission of rotation toward the guide wire tip can be ensured to raise the performance of penetration, because the middle connector 17 and the distal end connector 15 firmly attach the core elongated component 12 to the helical coil 13 at a small distance to the guide wire tip.

As the distal shaft diameter d2 is determined equal to or greater than a diameter of the coil filament 14a, the strength can be kept without lowering. Specifically, the minimum diameter of the turns of the helical coil 13 is equal to or less than three (3) times as much as the diameter of the coil filament 14a. Should the minimum diameter be still smaller, tensile stress occurs at points of the outer side of turns, because the length ratio of the coil filament 14a increases between the inner side and the outer side. A surface of strands of the helical coil 13 will be roughened in a scale shape. The helical coil 13 may break or damage according to insufficient strength.

As the tapered portion length L1 of the diameter decreasing coil portion 13b of the helical coil 13 is equal to or more than 25 mm, the helical coil 13 can be suitable for treatment of a diffuse lesion in a blood vessel. In contrast with the length of 10-15 mm of a lesion of a general type, a length of the diffuse lesion is very likely to be 20 mm or more. Should the tapered portion length L1 of the diameter decreasing coil portion 13b be smaller than 25 mm, the equiradial portion on the proximal side may jam in a lesion of the hard material or plaque. The value of 25 mm for the tapered portion length L1 is for sufficiency of the length in view of suitability for the diffuse lesion.

In FIG. 2, the tapered portion length L1 of the helical coil 13 is 25 mm. The length L0 from the guide wire tip to the middle connector 17 is 50 mm. Rotational transmission of force from the proximal side to the distal side is approximately 1.29 times higher than an example in a fully equiradial helical shape. Thus, the force can be rotationally transmitted with higher efficiency. A torsion angle of the helical coil 13, which changes inversely proportional to the spring constant, can be reduced in the invention. The rotational force can be transmitted to the guide wire tip only with a small force or small angle rotationally. Performance of penetration can be high.

The distal end diameter D2 of the helical coil 13 is three (3) or more times as much as the filament diameter t1 of the coil filament 14a for the purpose of preventing roughening of the surface and lowering of the strength. For example, the filament diameter t1 of the coil filament 14a is 0.065 mm. The diameter d2 of the core elongated component 12 is 0.065 mm. The distal end diameter D2 of the helical coil 13 is 0.195 mm. A surface pressure of a guide wire tip 19 per unit area of the end surface decreases when the distal end diameter D2 becomes more than 0.295 mm, so performance of penetration becomes lower. As the medical guide wire 10 is used in a catheter as a guiding tool for a balloon catheter, an inner diameter of the medical guide wire 10 is 0.360 mm for treatment of the coronary artery under the condition limited by the inner diameter of the catheter. Thus, the diameter ratio D1/D2 of the diameter decreasing portion is determined equal to or more than 1.22 (=0.360/0.295) and equal to or less than 1.85 (=0.360/0.195), to obtain higher performance of penetration without lowering the strength.

In FIG. 2, a second embodiment is illustrated. The first embodiment is repeated with a difference in that a tapered portion length L1 of the helical coil 13 is 32 mm. A length L2 of a region of the equiradial coil portion 13a extending to the middle connector 17 is 18 mm. A third embodiment is also constructed. The second embodiment is repeated with a difference in that the length L2 is 6 mm.

As the length L2 is 18 mm, a spring constant is approximately 1.37 times as high as that of a helical coil of a fully equiradial form. In contrast with the first embodiment having the ratio L1/L2=1/1 between the diameter decreasing coil portion 13b and the equiradial coil portion 13a, the second embodiment has a ratio L1/L2=1/1.7. The spring constant increases owing to the increase in the tapered portion length L1.

In the third embodiment, as the length L2 is 6 mm, a spring constant is approximately 1.5 times as high as that of a helical coil of a fully equiradial form. The torsion angle and the spring deflection decrease because the spring constant increases. Also, the middle connector 17 is attached to the equiradial coil portion 13a. There is no point of attachment to the diameter decreasing coil portion 13b being inclined. No unwanted flow of paraffin wax occurs on the diameter decreasing coil portion 13b. So operation of dispensing paraffin wax can be carried out stably. Furthermore, strength of attachment with the core elongated component can be kept from lowering, because flowing away of paraffin wax is prevented.

Figure 6:
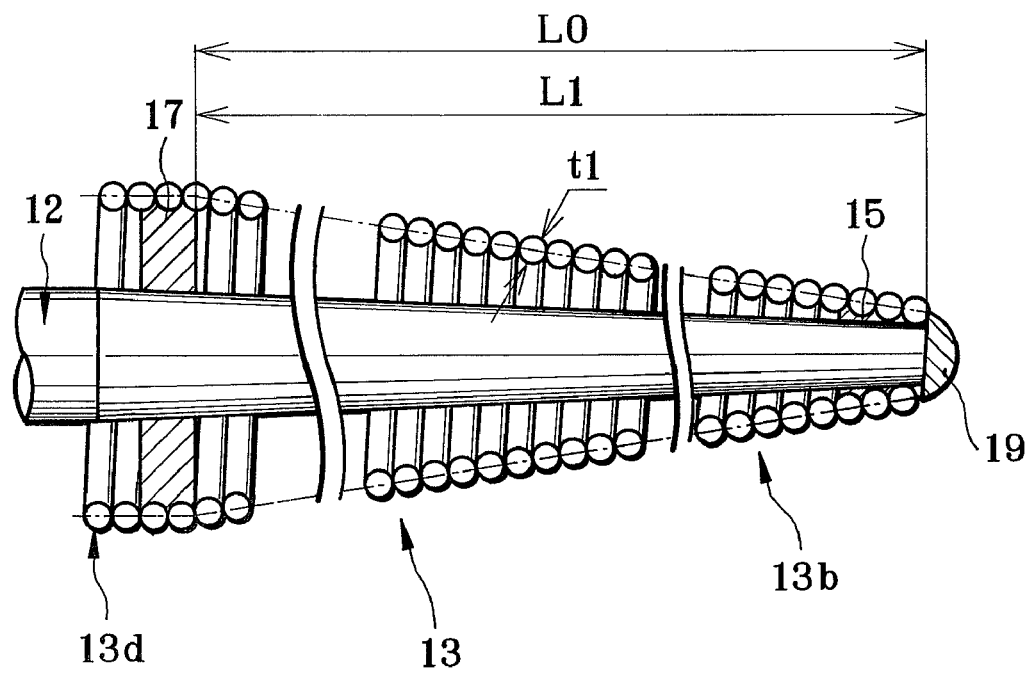
FIG. 6 is an explanatory view in section illustrating a fourth embodiment in which a middle connector is positioned between a diameter decreasing coil portion and an equiradial helical coil part.

A fourth embodiment is illustrated in FIG. 6. The first embodiment is repeated with a difference in that the equiradial coil portion 13a, which is positioned near to a proximal end of the diameter decreasing coil portion 13b having its greatest diameter, is associated with the middle connector 17 with paraffin wax. L2=0 mm. The tapered portion length L1 is equal to or more than 25 mm and equal to or less than 50 mm. The position of attachment with the paraffin wax is effective in obtaining a highest spring constant, and reducing the torsional angle and an spring deflection. No equiradial portion exists in the helical coil 13 from the guide wire tip to the middle connector as the diameter decreasing coil portion 13b extends at the full length. A spring constant is approximately 1.59 times as high as that of a helical coil of a fully equiradial form. The spring constant of the embodiment is the highest among all of the embodiments herein. As has been described above, the torsional angle and the spring deflection are inversely proportional. When spring constant increases, the torsional angle and the spring deflection decrease. Note that the spring constant is determined according to an equation for a relationship between the spring constant and spring deflection, and a formula for determining spring deflection of fully equiradial helical coil springs and conical coil springs.

Figure 7A:
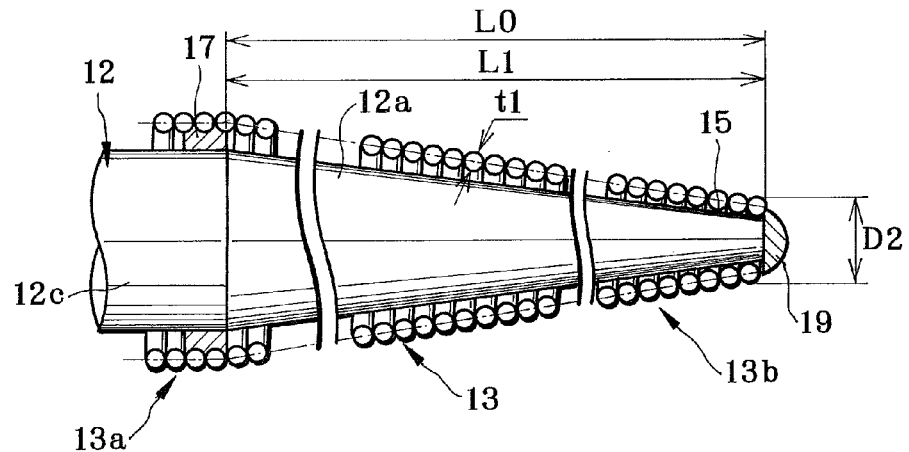
FIG. 7A is an explanatory view in section illustrating a fifth embodiment in which a tapered shaft portion extends to the guide wire tip.
Figure 7B:
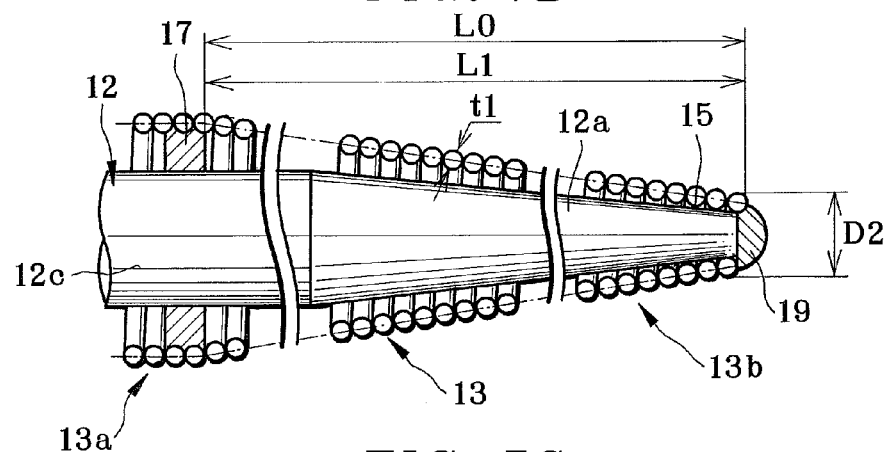
FIG. 7B is an explanatory view in section illustrating a sixth embodiment in which the middle connector is positioned on a small diameter shaft portion.
Figure 7C:
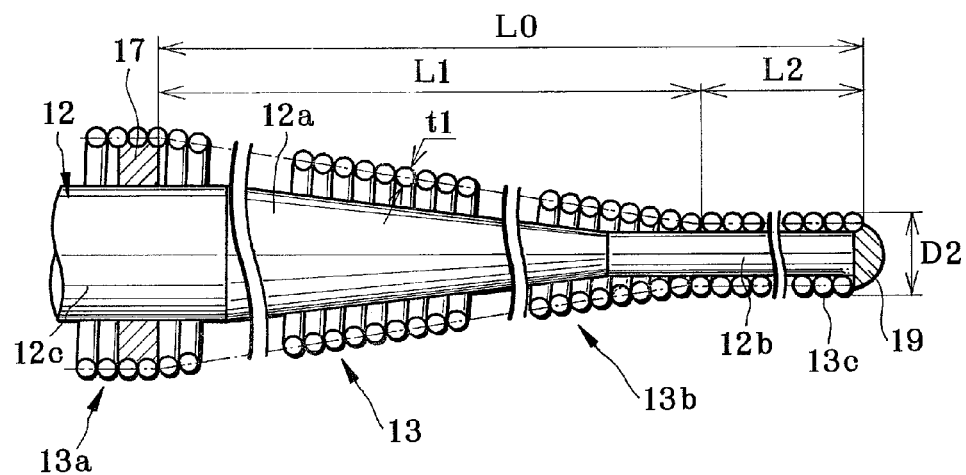
FIG. 7C is an explanatory view in section illustrating a seventh embodiment with an equiradial shaft end at a very small diameter.

In FIGS. 7A-7C, fifth, sixth and seventh embodiments are illustrated. The fourth embodiment is repeated with a difference of a tapered shape of the core elongated component 12. A portion of the core elongated component 12 positioned inside the diameter decreasing coil portion 13b of the helical coil 13 is tapered, to raise performance of rotational force to the guide wire tip. This is because the diameter of the core elongated component 12 can be great to extend to the inner diameter of a proximal end of the diameter decreasing coil portion 13b of the helical coil 13. Also, rotational transmission depends upon a length ratio between lengths or radii of radial portions.

Specifically, the distal end diameter D2 of the helical coil 13 is 0.253 mm. The distal shaft diameter d2 of the core elongated component 12 is 0.123 mm as the filament diameter t1 of the helical coil 13 is 0.065 mm. As the diameter D1 of the proximal side of the helical coil 13 is 0.360 mm, the proximal shaft diameter d1 of the core elongated component 12 is at most 0.230 mm. Rotational transmission of force from the proximal side to the distal side is approximately 1.87 times higher than an example in a regularly helical shape having the distal shaft diameter d2 of 0.253 mm in the core elongated component 12 because of 0.230/0.123. Thus, the force can be rotationally transmitted with higher efficiency.

A preferable range of the ratio d1/d2 of the tapered shaft portion 12a of the core elongated component 12 is from 1.10 to 2.64 in consideration of stability of the coil form, distal end strength, and high performance of rotational transmission. Specifically, the diameter of the core on the side of the proximal end connector 16 is 0.135 mm for the purpose of keeping rotational transmission and considering the flowing property of paraffin wax. The distal end diameter of the core elongated component is at most 0.123 mm (=0.253−0.065×2). The diameter ratio between the core portions is approximately 1.10. The diameter d2 of the equiradial shaft end 12b of the core elongated component 12 is 0.087 mm for the purpose of keeping stability of the coil form and strength of the core elongated component 12. The proximal shaft diameter d1 of the core elongated component 12 at the proximal end connector 16 is 0.230 mm (=0.360−0.065×2) or less. The diameter ratio d1/d2 is approximately 2.64 (=0.230/0.087). Note that the tapered shaft portion 12a can be shaped with a length corresponding to the diameter decreasing coil portion 13b of the helical coil 13 in the manner of FIG. 7A of the fifth embodiment. Also, the tapered shaft portion 12a of the core elongated component 12 can be formed shorter than the diameter decreasing coil portion 13b of the helical coil 13 in the manners of FIGS. 7B and 7C of the sixth and seventh embodiments, to facilitate insertion of the core elongated component 12 into the helical coil 13.

Figure 8:
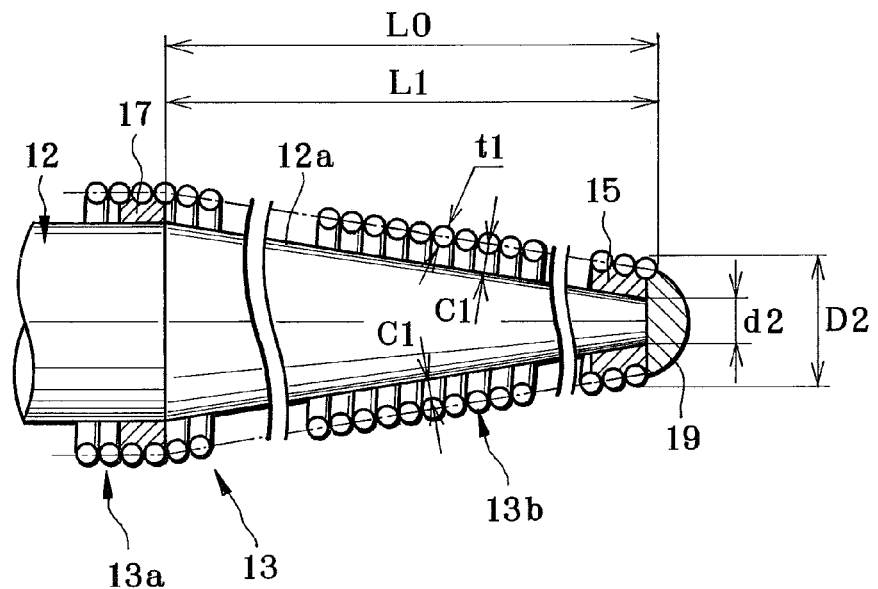
FIG. 8 is an explanatory view in section illustrating an eighth embodiment having a space between the core elongated component and the helical coil.

An eighth embodiment is illustrated in FIG. 8. The fourth embodiment is repeated with a difference in that a space C (=C1×2) is formed between the core elongated component 12 and the helical coil 13. The space C at the middle connector 17 of the helical coil 13 on the core elongated component 12 is ½ as much as the filament diameter t1 of the coil filament 14a.

In the eighth embodiment, a predetermined space C1 is defined between the core elongated component 12 and the helical coil 13, so intensity of attachment with the core elongated component 12 is ensured by higher flowability of paraffin wax into the space. The insertion of the core elongated component 12 into the helical coil 13 is facilitated to raise suitability for assembly. Performance of transmission of rotation to the core elongated component 12 can be high according to the high flowability and suitability for assembly. The distal end diameter D2 of the helical coil 13 is 0.253 mm. The filament diameter t1 of the helical coil 13 is 0.065 mm. Thus, the distal shaft diameter d2 is 0.0905 mm. As the proximal end diameter D1 of the helical coil 13 is 0.360 mm, and the proximal shaft diameter d1 of the core elongated component 12 is 0.1975 mm, rotational transmission of force from the proximal side to the distal side is approximately 2.18 times higher than an example in a regularly helical shape, because of 0.1975/0.0905.

The diameter ratio d1/d2 is equal to or more than 1.10 and equal to or less than 2.36. Thus, the stability of the helical shape can be kept with the strength of the tip of the core elongated component according to the fourth embodiment. Furthermore, performance of transmission of rotation can be higher in a similar manner to the coil spring tapered portion. Note that the diameter ratio d1/d2 is preferably equal to or more than 1.49 and equal to or less than 2.27 as a preferable range. The reason for this is described as follows.

In consideration of the rotational transmission to the distal end, the proximal shaft diameter d1 is 0.135 mm. The distal shaft diameter d2 is 0.0905 mm (=0.253−0.065×2.5). The diameter ratio d1/d2 is approximately 1.49 (=0.135/0.0905). In consideration of the stability of the coil shape and strength of the guide wire tip, the distal shaft diameter d2 is 0.087 mm. The proximal shaft diameter d1 of the proximal end connector 16 is 0.1975 (=0.360−0.065×2.5). The diameter ratio d1/d2 is approximately 2.27 (=0.1975/0.087). Thus, the diameter ratio d1/d2 is preferably equal to or more than 1.49 and equal to or less than 2.27.

Note that in the calculation, the factor of 2.5 is derived from a combination of two times the filament diameter of the coil filament 14a and the thickness of the space C.

Figure 9:
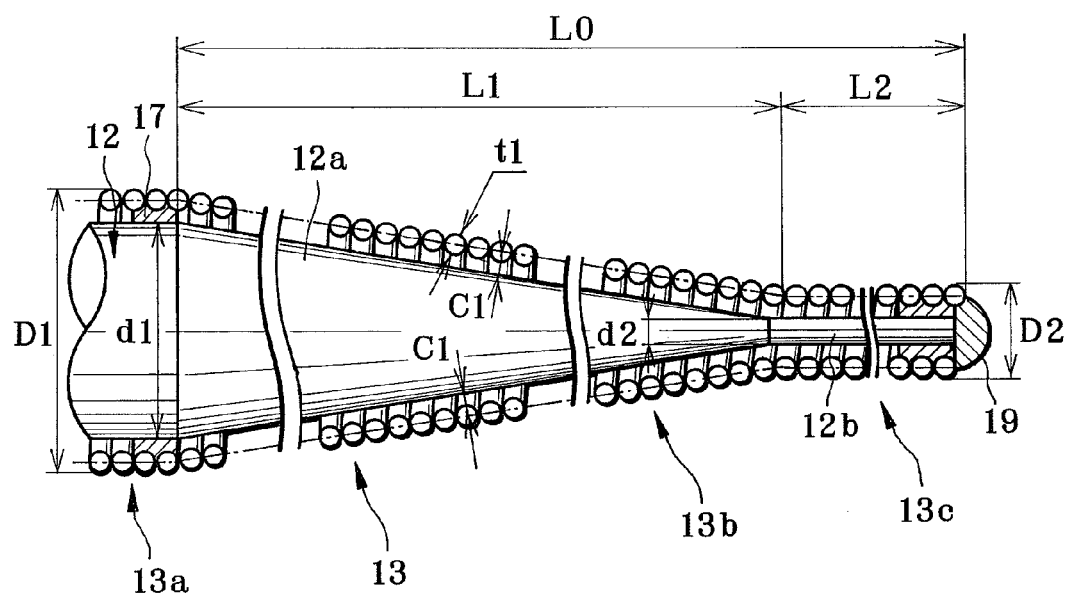
FIG. 9 is an explanatory view in section illustrating a ninth embodiment having an equiradial coil end.

A ninth embodiment is illustrated in FIG. 9. The eighth embodiment is repeated with a difference in that the equiradial coil end 13c is disposed as distal end of the helical coil 13. The equiradial coil end 13c has a diameter equal to the first diameter D2 of the diameter decreasing coil portion 13b on the distal side. A ratio L1/L3 of the tapered portion length L1 to the equiradial portion length L3 is equal to or more than 3.1 and equal to or less than 7.3.

Figure 10A:
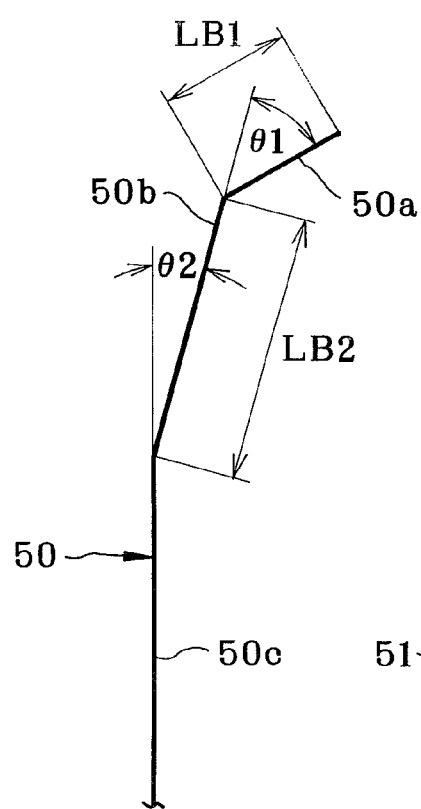
FIG. 10A is an explanatory view illustrating articulating bends of the guide wire.
Figure 10B:
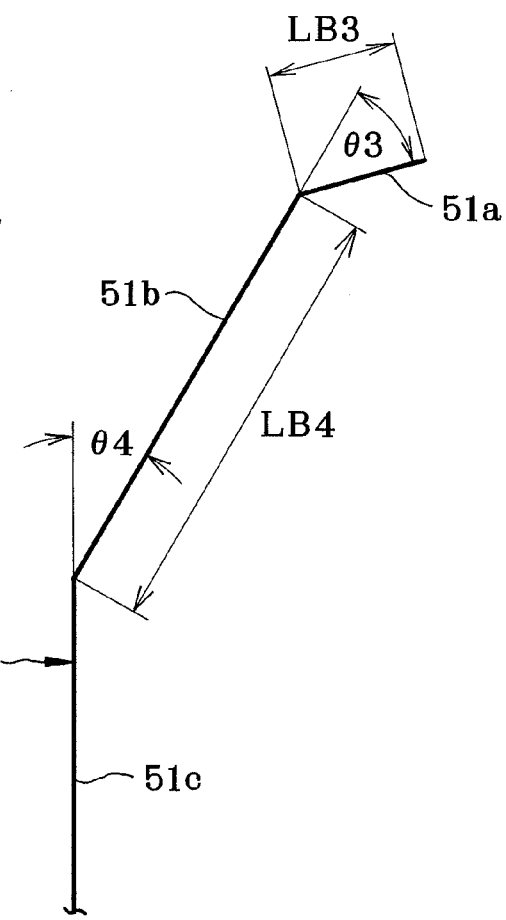
FIG. 10B is an explanatory view illustrating articulating bends of another preferred guide wire.

Thus, the steerable property can be higher to reach a true lumen of a lesion of the vessel, as the equiradial coil end 13c is additionally disposed on the diameter decreasing coil portion 13b. In general, a plurality of guide wires are prepared and used for selective purposes of types of blood vessels. For example, guide wire tips are curved. Also, in FIGS. 10A and 10B, articulating bends 50a, 50b, 51a and 51b are provided in guide wires, and have two bent forms. When medical guide wires 50 and 51, having a guide wire tip with high rigidity, is used in the above-described parallel guide wire technique for a total occlusion in intravascular treatment, the medical guide wire 51 is constructed with a different guide wire tip from that of the medical guide wire 50. This is effective in reaching a true lumen by guiding the tip of the medical guide wire 51 in a direction different from the medical guide wire 50. Specific parameters are changed for the state of lesions, including an angle $\theta 1$ defined between the articulating bends 50a and 50b, an angle $\theta 3$ defined between the articulating bends 51a and 51b, an angle $\theta 2$ defined between the articulating bend 50b and a guide wire body 50c, and an angle $\theta 4$ defined between the articulating bend 51b and a guide wire body 51c, and lengths LB1-LB4 of the bends. For example, $\theta 1$ is 45 degrees, $\theta 2$ is 15 degrees, $\theta 3$ is 45 degrees, $\theta 4$ is 30 degrees, LB1 is 2 mm, LB2 is 4 mm, LB3 is 2 mm and LB4 is 6 mm. Also, the total length LB5 (=LB1+LB2 or LB3+LB4) is equal to or less than 8 mm. A micro catheter is extended to each of points of bends particularly for the structure with the two bends. Shapes of the bends are selected for use in the treatment of blood vessels.

In relation to constructing the articulating bends 50a and 50b or the articulating bends 51a and 51b, the tendency of bending can be easily imparted if a shape of a region of bending is equiradial. If the shape of a bending region is tapered, rigidity changes gradually at each of points of bending, so that a difficulty is higher in determining the bending position in comparison with the equiradial shape. A length ratio between the equiradial coil end 13c and the diameter decreasing coil portion 13b is equal to or more than 3.1 and equal to or less than 7.3. Specifically, when the equiradial portion length L3 of the equiradial coil end 13c is 8 mm, the minimum size of the tapered portion is 25 mm. A ratio L1/L3 is 25/8=3.1. As the equiradial portion length L3 is 6 mm, the tapered portion length L1 is 44 mm. A ratio L1/L3 between those is 44/6=7.3. Thus, it is preferable that the ratio L1/L3 between the diameter decreasing coil portion 13b and the equiradial coil end 13c is equal to or more than 3.1 and equal to or less than 7.3. The equiradial coil end 13c is effective in ensuring the flexibility of the guide wire tip, because the region of the small diameter is kept sufficient by the equiradial coil end 13c in comparison with the totally tapered structure.

Figure 11:
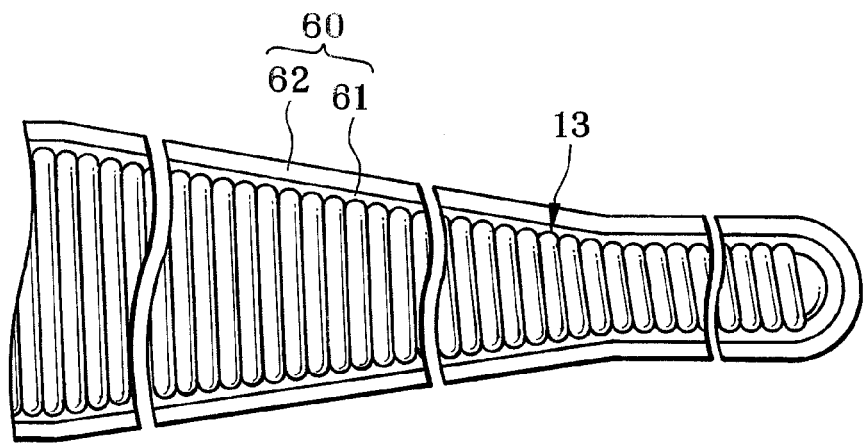
FIG. 11 is an explanatory view illustrating a tenth embodiment with a helical coil coated with a lubricant coating.

In FIG. 11, a tenth embodiment is illustrated. The ninth embodiment is repeated with a difference in that a lubricant coating 60 is applied on the peripheral surface of the helical coil 13. Characteristically, the lubricant coating 60 comes to have lubricating property when wetted. A hydrophobic coating layer 61 is formed on the outer surface of the helical coil 13. After this, a coating layer 62 of hydrophilic polymer is formed on the hydrophobic coating layer 61. The hydrophobic coating layer 61 and the hydrophilic coating layer 62 are combined to constitute the lubricant coating 60. As the helical coil 13 is tightly wound, the hydrophobic material does not enter the space between strands of the helical coil 13 even in application of the coating of the hydrophobic material. The hydrophobic material can coat the surface of the helical coil 13 in a sufficiently smooth manner. Then a coating of the hydrophilic polymer is applied to the hydrophobic coating layer 61, to form the hydrophilic coating layer 62. The double structure of the coating layers makes the outer surface smooth. High smoothness can be obtained in comparison with loosely wound helical coils. Examples of the hydrophobic materials include polyurethane, polyamide, fluorocarbon resin and the like. Examples of hydrophilic materials include polyvinyl pyrolidone, polyethylene oxide, anhydride of maleic acid ethyl ester, and the like.

An eleventh embodiment is described now. The first embodiment of FIG. 2 is repeated with a difference in that the diameter D1 of the helical coil 13 on the proximal side is 0.450 mm or less, and that the ratio D1/D2 between the diameters D1 and D2 on the proximal and distal sides is equal to or more than 1.52 and equal to or less than 2.31. The eleventh embodiment is constructed as a guide wire for treatment of blood vessels in lower extremities. The eleventh, twelfth and thirteenth embodiments are disclosed for this common purpose.

There is a reason of enlarging the diameter D1 of the helical coil 13. To introduce a treatment tool into the lesion of an occlusion of a vessel of lower extremities, it is preferable to insert the tool through an upper thigh near to the lesion. However, there is a problem in requiring long time for hemostasis of blood because of the great diameter of the vessel of the lesion. Ischemia is likely to occur. Another technique of treatment is to approach the lower extremities through an arm. A treatment tool is introduced through the arm, passed through the arch of aorta and then an abdominal aorta to reach the occlusion of a peripheral artery of the lower extremities for treatment. It is necessary for a treatment tool to have flexibility for passage through the arch of aorta with a long path, and penetrability sufficient for reaching a target lesion.

In general, a vessel diameter of a lesion in the vessels of lower extremities is relatively greater than a vessel diameter of a lesion of the coronary artery. A length of the occlusion at the lesion in the vessels of lower extremities is also greater than that of the coronary artery. To be precise, the vessel diameter of the coronary artery is 2-3 mm. The vessel diameter of the lesion in the vessels of lower extremities is 4-6 mm in regions higher than the knee joint, and 2-4 mm in regions lower than the knee joint. There are some exceptions according to specificity and differences between portions of lesions. A length of a diffuse lesion is 20 mm at the lesion of the coronary artery, but is 100 mm or more at the lesion in the vessels of lower extremities. Variants may exist according to specificity and differences between portions of lesions.

Therefore, a guide wire should be constructed by considering a path to approach a lesion, vessel diameter, and lesion length. The guide wire for lower extremities requires penetrability, and should have a greater diameter than that for treatment of a coronary artery.

The diameter of the helical coil 13 is equal to or less than 0.450 mm. The ratio D1/D2 is in a range of 1.52-2.31. This is because the proximal shaft diameter d1 of the core elongated component 12 in the helical coil 13 can be greater by raising the diameter D1 of the helical coil 13 on the proximal side. As the diameter D1 rises from the 0.360 mm to the 0.450 mm, the diameter of the core elongated component 12 can be greater in association with this. The flexural rigidity can be approximately 2.4 times higher because the flexural rigidity is proportional to the geometrical moment of inertia. Thus, the suitability for penetration can be better.

When the diameter D2 is more than 0.295 mm, a surface pressure of the guide wire tip 19 per unit area becomes lower to lower the penetrating property. For use with a balloon catheter, the medical guide wire 10 in the balloon catheter of a widely manufactured type has the maximum diameter of 0.450 mm. Thus, the diameter ratio D1/D2 is equal to or more than 1.52 (=0.450/0.295) and equal to or less than 2.31 (=0.450/0.195). As an important feature of the invention, the diameter ratio D1/D2 is equal to or more than 1.22 and equal to or less than 2.31, as a result of combining the first embodiment with the diameter ratio D1/D2 of 1.22-1.85, and the eleventh embodiment with the diameter ratio D1/D2 of 1.52-2.31.

The medical guide wire 10 for vessels of lower extremities requires flexibility and penetrability. The flexibility is suitability for passing the arch of aorta with a large bend even after percutaneously introducing through an artery of an arm, the penetrability being suitability for passing the arch of aorta and then the abdominal aorta to reach a target region of the peripheral artery to be treated. After the reach to the peripheral artery, high performance of penetration can be obtained according to the tapered shape of the helical coil.

A twelfth embodiment is constructed. The eleventh embodiment is repeated with a difference of the diameter ratio D1/D2 equal to or more than 1.52 and equal to or less than 2.31. Also, the diameter ratio d1/d2 of the core elongated component 12 is equal to or more than 1.10 and equal to or less than 3.68. This is based on the same reason as the fourth embodiment. The diameter of the helical coil is considered.

$$d1/d2=0.135/(0.253-0.065\times 2)=1.10; \text{ and}$$

$$d1/d2=(0.450-0.065\times 2)/0.087=3.68$$

A thirteenth embodiment is described now. The eleventh embodiment is repeated with a difference in that the equiradial coil end 13c is positioned on the distal side of the diameter decreasing coil portion 13b of the helical coil 13. A ratio L1/L3 of the tapered portion length L1 to the equiradial portion length L3 is equal to or more than 3.1 and equal to or less than 24. Specifically, the minimum value of the tapered portion length L1 is 25 mm when the equiradial portion length L3 is 8 mm. The ratio L1/L3 between those is 3.1 (=25/8). Also, the maximum value of the tapered portion length L1 is 48 mm when the equiradial portion length L3 is 2 mm. The ratio L1/L3 between those is 24 (=48/2). Accordingly, it is preferable in the invention that the ratio L1/L3 is 3.1-24 because of a range of 2-8 mm of the equiradial portion length L3.

The equiradial coil end 13c is disposed on the diameter decreasing coil portion 13b. The length ratio L1/L3 of the helical coil 13 is equal to or more than 3.1 and equal to or less than 7.3. The tapered portion length L1 of the diameter decreasing coil portion 13b is 25 mm as the equiradial portion length L3 is 8 mm. The length ratio L1/L3 is 3.1 (=25/8). Further, the tapered portion length L1 of the diameter decreasing coil portion 13b is at least 44 mm as the equiradial portion length L3 is 6 mm. The length ratio L1/L3 is 7.3 (=44/6). Accordingly, the length ratio L1/L3 is equal to or more than 3.1 and equal to or less than 7.3. The present example can have a higher flexibility of the guide wire tip than the structure in a fully tapered shape, because the small diameter portion is defined by the equiradial coil end 13c with a sufficient length. Note that it is possible for an operator to select one of the twelfth and thirteenth embodiments according to an observed state of a lesion. In a similar manner to the tenth embodiment, it is preferable in the eleventh, twelfth and thirteenth embodiments to apply the lubricant coating 60 on the periphery of the helical coil 13 in a region extending to the proximal connector for the lubricating property when wetted.

In the above embodiment, the helical coil 13 is the monofilament helical coil of which a single filament is wound. However, the helical coil 13 may be the plural filament helical coil in which plural filaments are wound in a coil form. In the plural filament helical coil, diameters of the plural filaments may be equal to one another, or can be difference from one another. The use of the plural filaments in the plural filament helical coil is effective in having a high tensile strength and higher safety. Also, a shape with a recess or protrusion in the plural filament helical coil makes it possible to impart high performance of penetration to the helical coil 13.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A medical guide wire comprising:
   a flexible long core;
   a core elongated component, disposed to extend forwards from an end of said core, having a tapered shape;
   a helical coil, disposed about said core elongated component, secured by attachment of a coil distal end and a coil proximal end to said core elongated component; and
   a guide wire tip, positioned at a distal end, and having one portion of said core elongated component and said coil distal end of said helical coil attached to said core elongated component;
   wherein said helical coil comprises:
   an equiradial coil portion, having said coil proximal end, disposed at a portion of said core elongated component on a side of said core;
   a diameter decreasing coil portion, having said coil distal end, disposed to extend forwards from said equiradial coil portion, having a decreasing diameter, and having a length equal to or more than 25 mm; and
   a middle connector, disposed at a distance equal to or less than 50 mm from said coil distal end, for attaching said helical coil to said core elongated component;
   wherein said helical coil has a coil filament having a constant diameter with strands tightly wound in a range from said coil distal end to said middle connector;
   a diameter ratio D1/D2 of said diameter decreasing coil portion is equal to or more than 1.22 and equal to or less than 2.31, where D1 is a diameter of said diameter decreasing coil portion on a side of said coil proximal end, and D2 is a diameter of said diameter decreasing coil portion on a side of said coil distal end;
   said core elongated component and said helical coil satisfy a condition of d2>t where d2 is a diameter of a distal end of said core elongated component, and t is a filament diameter of said coil filament; and
   one end of said diameter decreasing coil portion nearer to said equiradial coil portion is disposed at said middle connector.

2. The medical guide wire of claim 1, wherein the middle connector is positioned at the proximal end from a point defined between the diameter decreasing coil portion and the equiradial coil portion.

3. The medical guide wire of claim 1, wherein a length ratio L1/L2 of the helical coil is equal to or more than 1, where L1 is a length of the diameter decreasing coil portion, and L2 is a length of the equiradial coil portion extending to the middle connector.

4. The medical guide wire of claim 1, wherein the diameter decreasing coil portion has a diameter decreasing in a range extending to the guide wire tip.

* * * * *